United States Patent [19]

Chu

[11] Patent Number: 5,585,183

[45] Date of Patent: Dec. 17, 1996

[54] PREPARATION OF LIQUID-CORE MICROCAPSULES FOR CELL CULTURES

[75] Inventor: I-Ming Chu, Hsinchu, Taiwan

[73] Assignee: National Science Council, China

[21] Appl. No.: 226,874

[22] Filed: Apr. 13, 1994

[51] Int. Cl.⁶ ............................. B32B 5/16; B32B 9/00; B32B 15/02; B32B 17/02
[52] U.S. Cl. ................. 428/402.2; 435/178; 435/182; 435/240.22; 435/289.1; 424/DIG. 7
[58] Field of Search ................... 428/402.2; 435/178, 435/182, 420; 424/DIG. 7, 93

[56] References Cited

U.S. PATENT DOCUMENTS

| | | | |
|---|---|---|---|
| 4,352,883 | 10/1982 | Lim | 435/178 |
| 4,407,957 | 10/1983 | Lim | 435/178 |
| 4,409,331 | 10/1983 | Lim | 435/178 |

*Primary Examiner*—Nathan M. Nutter
*Attorney, Agent, or Firm*—Fish & Richardson P.C.

[57] ABSTRACT

A method for preparing liquid-core microcapsules for cell cultures, using a hardening solution containing $CaCl_2$ and polyethyleneimine to harden gel-core beads before coating them with polylysine solution.

16 Claims, 6 Drawing Sheets

PREPARATION OF LIQUID-CORE MICROCAPSULES FOR CELL CULTURES

BACKGROUND OF THE INVENTION

The present invention relates to a method for preparing liquid-core microcapsules for cell cultures, and in particular to a method for preparing liquid-core microcapsules for cell cultures, which uses a hardening solution containing $CaCl_2$ and polyethyleneimine to harden gel-core beads before coating them with polylysine solution.

When culturing high-density animal cells, the use of liquid-core microcapsules has many advantages, for example, low cost, ease of culturing and high suitability for culturing various animal cells. Due to the strict requirements on the growing conditions for animal cell cultures, when the microencapsulation technique is used for culturing animal cells, the materials selected for the microcapsules and the method of encapsulation are usually more stringent than the fixing conditions of the cells.

T. Yoshioka et al disclose a process for producing liquid-core microcapsules, which involves adding a polyelectrolyte compound dropwisely to another polyelectrolyte compound of opposite charge (*Biotechnol. Bioeng.* Vol. 35, pp 66, 1990).

M. C. Bane et al disclose microcapsules made of a new synthetic polymer (*Biotechnol. Bioeng.* Vol. 9, pp 468, 1991). S. Iijima et al disclose a method for producing gel-core microcapsules by using interfacial polymerization wherein the gel-core contains alginate and polyurea (*Appl. Microbiol. Biotechnol.* Vol. 28, pp 572, 1988).

In the high-density culturing of animal cells, using liquid-core microcapsules can provide larger growing space for the animal cells encapsulated therein as compared to gel-core microcapsules, and thereby provide higher production. However, as some liquid-core microcapsules are fragile, when the culturing is conducted in a large scale culture device, they are easily ruptured due to mechanical collisions caused by necessary stirring and aeration, causing leakage of the cells and accordingly affecting the whole manufacturing process thereof. E. R. Mckillip et al have reported the problems encountered when cells are mass-cultured by using liquid-core microcapsules (*Bio./Technol.*, Vol. 9, pp 805, 1991).

Heretofore liquid-core microcapsules are produced by mixing a 1–3% alginate solution as core material with cultured cells to form a mixture, dropping the mixture into a 1–3% $CaCl_2$ solution (hardening solution) to gel the mixture to form gel-core beads, placing the gel-core beads in a solution containing 0.1% of polylysine or polyethyleneimine to coat the beads and form a membrane thereon, followed by dissolving the calcium ion in the gel cores with sodium citrate. The resulting liquid-core microcapsules, when used in culture of animal cells, are able to produce $10^8$ cells per ml. However, they have the following disadvantages:

(1) The lifetime of the liquid-core microcapsules is only 2 weeks when they are used for animal cell culture due to their weak mechanical strength.

(2) In accordance with the conventional processes, the operating time for each step influences the quality of the final microcapsules greatly. For example, assuming the coating time of polylysine is set at 3 minutes, increasing or reducing the coating time will result in the instability of the resulting liquid-core microcapsules. Therefore, according to the above-mentioned conventional manufacturing process, when mass production is desired, it is difficult to obtain liquid-core microcapsules having controlled quality.

(3) If cells capable of producing high molecular weight proteins (MW$\geq$160 Kd), for example, monoclonal antibodies, are encapsulated in liquid-core microcapsules prepared by the above conventional method, as the produced protein can not permeate the microcapsule membrane and therefore can not be released therefrom, the continuous production of the cells will be hindered.

Gel-core microcapsules made of alginate and polyurea as proposed by S. Iijima et al can overcome a part of the above disadvantages, however, they have the disadvantage that the cell density is low, and can not reach the value of $10^8$ cells per ml.

SUMMARY OF THE INVENTION

It is therefore an object of this invention to provide a method for preparing liquid-core microcapsules obviating the above-mentioned disadvantages.

To attain the above object, it has now been found that dropping a solution containing $CaCl_2$ and polyethyleneimine as hardening agent into a mixture of cultured cells and core material including alginate and optionally carboxymethyl cellulose to form gel-core beads, followed by coating them with polylysine solution can produce liquid-core microcapsules having superior mechanical stability that are capable of producing high density cells and allowing the produced cells to be released, and can make more flexible the operating time for each step of manufacturing liquid-core microcapsules, for example coating with polylysine.

More specifically, the method for the preparation of liquid-core microcapsules according to the invention includes adding a core material solution dropwisely to cultured cells in a culture medium to form a mixture, wherein the core material solution is a solution of alginate; adding the mixture to a hardening solution containing $CaCl_2$ and polyethyleneimine to form gel-core beads; coating the gel-core beads with polylysine solution; and dissolving the coated gel-core beads with citrate salts to form the liquid-core microcapsules. The microcapsules prepared by this method, for the ease of description, hereinafter are refered to as Type A microcapsules.

Alternatively, liqid-core microcapsules can be produced by adding a core material solution to cultured cells in a culture medium to form a mixture, wherein the core material solution is a solution of alginate and carboxylmethyl cellulose; adding the mixture to a hardening solution containing $CaCl_2$ and polyethyleneimine to form gel-core beads; and coating the gel-core beads with polylysine solution to form the liquid-core microcapsules. The microcapsules prepared by this method are hereinafter referred as Type B microcapsules.

BRIEF DESCRIPTION OF THE DRAWINGS

The present invention will be described in detail with reference to the illustrative examples and the accompany drawings, in which.

DETAILED DESCRIPTION OF THE INVENTION

According to the invention, core material suitable for use in the method includes alginate or carboxylmethyl cellulose, because they are polyelectrolyte compounds and thus have good physiological compatability with animal cells, are nontoxic and are able to form stable nonsoluble microcapsules under mild conditions. The core material should be in the form of a solution when used. According to the present invention, in the prepartion of Type A microcapsules, only alginate is used as the core material, and the concentration should be in the range of 0.2 to 1.0 percent by weight, preferably 0.9 percent by weight. In the preparation of Type B microcapsules, a mixture of alginate and carboxulmethyl cellulose is used as the core material. The core material solution is added to the cultured cells contained in culture medium to form a mixture. The amount of the core material usually is 5 to 10 times that of the total amount of cultured cells and culture medium.

The hardening solution of the invention contains $CaCl_2$ and polyethyleneimine (PEI). The concentration of $CaCl_2$ should be in the range of from 1 to 3, preferably 1.5 percent by weight and the concentration of PEI should be in the range of from 0.1 to 1.5, preferably 0.5 percent by weight. The core material mixture is dropped into the hardening solution to form gel-core beads.

To reinforce the mechanical stability of the formed gel-core beads, according to the method of the invention, coating with polylysine is necessary. The coating is conducted by immersing the gel-core beads into polylysine solution. The concentration of the polylysine should be in the range of from 0.05 to 1.0 percent by weight.

According to the method of the invention, if only alginate is used as the core material, that is, in the case of preparing Type A microcapsules, the resulting gel-core beads should further be treated with citrate salts, for example sodium citrate, to dissolve the gel-cores to form the liquid-core microcapsules. However, if a mixture of alginate and polyethyleneimine is used as core material, as in the Type B microcapsules, it is not necessary to use citrate salts to dissolve the gel-cores because the content of the alginate is very low, for example 0.2 percent by weight, and therefore will be easily dissolved by phosphate which are usually included in culture medium for the cultured cells, to form liquid-core microcapsules.

The invention is more specifically described by the following illustrative examples.

Example 1

Solutions containing respectively the core materials of the invention as set forth in Table 1 were dropped into hardening solutions having the compositions as set forth in Table 1. Gel-core beads were formed and tested for mechanical stability (mechanical strength). The test was conducted by placing the beads in a 50 mM citrate solution and observing. The gel-core beads are deemed stable if no rupture was observed within 10 minutes. The test results are summarized in Table 1.

The same procedures as Example 1 were repeated except the core materials used were alginate and dextran sulfate having concentrations as set forth in Table 1. The test results are also summarized in Table 1.

TABLE 1

| Core Material | Hardening Solution | | | | | | | | | |
|---|---|---|---|---|---|---|---|---|---|---|
| | CaCl₂ 2.5% | | | | | CaCl₂ 1.5% | | | | |
| | DEAE-dextran | | PEI | | PLL | DEAE-dextran | | PEI | | PLL |
| | 1.0% | 0.5% | 1.0% | 0.5% | 0.05% | 1.0% | 0.5% | 1.0% | 0.5% | 0.05% |
| alginate | | | | | | | | | | |
| 1.0% | − | − | + | + | − | − | − | + | + | − |
| 0.7% | − | − | + | + | − | − | − | + | + | − |
| 0.5% | − | − | + | + | − | − | − | + | + | − |
| alginate/CMC | | | | | | | | | | |
| 0.5%/1.0% | − | − | + | + | − | − | − | + | + | − |
| 0.5%/0.5% | − | − | + | + | − | − | − | + | + | − |
| alginate/dextran sulfate | | | | | | | | | | |
| 0.5%/1.0% | − | − | + | + | − | − | − | + | + | − |
| 0.5%/0.5% | − | − | + | + | − | − | − | + | + | − |

+: stable in 50 mM citrate solution for at least 10 min
−: ruptured within 10 min in 50 mm citrate solution.

As can be seen from the results of Table 1, including polyethyleneimine in addition to $CaCl_2$ in the hardening solution can increase the mechanical stability of the gel-core beads.

Example 2

Solutions containing the core materials of the invention as set forth in Table 2 were dropped into a hardening solution containing 1.5 percent by weight of $CaCl_2$ and 0.5 percent by weight of polyethyleneimine. Gel-core beads were formed. The formed gel-core beads were then coated with polylysine, polyethyleneimine and DEAE-dextran at concentrations indicated in Table 2, and tested for the mechanical stability by the same method as in Example 1. The test results are summarized in Table 2.

The same procedures as Example 2 were repeated except the core materials used were alginate and dextran sulfate having concentrations as set forth in Table 2. The test results are also summarized in Table 2.

TABLE 2

| Core Material (wt %) | Coating Material | | |
|---|---|---|---|
| | polylsine 0.05% | polyethyl-eneimine 0.1% | DEAE-dextran 0.1% |
| alginate | | | |
| 0.7% | + | − | − |
| 0.5% | + | − | − |
| alginate/CMC | | | |
| 0.5%/1.0% | + | + | − |
| 0.5%/0.5% | + | + | − |
| alginate/DS | | | |
| 0.5%/1.0% | + | − | − |
| 0.5%/0.5% | + | − | − |

+: stable in citrate solution for at least 10 min
−: ruptured within 10 min in citrate solution As can be seen from the results of Table 2, adding polyethyleneimine into hardening solution followed by coating with a layer of polylysine can enhance the mechanical strength of the formed gel-core beads.

Example 3

Solutions containing the core materials as set forth in Table 3 were dropped into hardening solutions having the compositions as set forth in Table 3. Gel-core beads were formed and then coated with 0.05 percent by weight of polylysine solution and washed with 20 mM, pH 7 sodium citrate solution for 10 minutes and tested for mechanical stability (mechanical strength). The test was conducted by placing the beads in a 20 mM phosphate solution and shaking it with a shaker at a rate of 200 rpm with an amplitude of 8 cm for 24 hours or 48 hours. The test results are summarized in Table 3.

TABLE 3

| | Hardening Solution $CaCl_2$ (wt %) | | | | | | | | |
|---|---|---|---|---|---|---|---|---|---|
| Core | 2.5% | | | 1.5% | | | 1.0% | | |
| Alginate | polyethyleneimine, PEI (wt %) | | | | | | | | |
| (wt %) | 0 | 0.5 | 1.0 | 0 | 0.5 | 1.0 | 0 | 0.5 | 1.0 |
| 0.9% 24 hr | 0 | 98 | 99 | 0 | 98 | 98 | 0 | 96 | 93 |
| 48 hr | 0 | 93 | 90 | 0 | 97 | 91 | 0 | 95 | 93 |
| 0.7% 24 hr | 0 | 97 | 99 | 0 | 98 | 99 | 0 | 94 | 94 |
| 48 hr | 0 | 92 | 96 | 0 | 93 | 96 | 0 | 91 | 90 |
| 0.5% 24 hr | 0 | 96 | 100 | 0 | 100 | 100 | 0 | 90 | 100 |
| 48 hr | 0 | 88 | 100 | 0 | 97 | 99 | 0 | 85 | 99 |

*the numeral indicates the percent of gel-core beads remaining unruptured after the shaking test As can be seen from Table 3 that all the gel-core beads coated with a hardening solution without polyethyleneimine ruptured and 90 percent of the gel-core beads coated with hardening solution containing both $CaCl_2$ and polyethyleneimine remained unruptured.

The same gel-core beads were prepared by following the same procedures as Example 3 except that no coating with polylysine were applied to the formed gel-core beads. The resulting gel-core beads were also tested by the same method. All gel-core beads without the polylysine coating ruptured.

Example 4

Gel-core beads were prepared by following the procedures of Example 3 except that the concentration of polyethyleneimine, the hardening time and the coating time used are set forth in Table 4. The prepared gel-core beads were tested for their mechanical stability by the same method as Example 3 for 48 hours. The test results are summarized in Table 4.

TABLE 4

| polyethyl-eneimine (wt %) | hardening time (minutes) | coating time (minutes) | | |
|---|---|---|---|---|
| | | 6 | 10 | 15 |
| 0.1% | 6 | 0 | 0 | 15 |
| | 10 | 0 | 98 | 41 |
| | 15 | 31 | 75 | 80 |
| 0.5% | 6 | 0 | 0 | 17 |
| | 10 | 50 | 97 | 87 |
| | 15 | 55 | 55 | 94 |
| 1.0% | 6 | 0 | 0 | 10 |
| | 10 | 47 | 98 | 90 |
| | 35 | 75 | 70 | 96 |

*the numeral indicates the percent of gel-core beads remaining unruptured after the shaking test As can be seen from Table 4 that if both the hardening time and the coating time exceed 10 minutes, most of the prepared gel-core beads remain unruptured.

Example 5

Gel-core beads were prepared by using 0.2 wt % alginate, 1.2 wt % carboxylmethyl cellulose as core material, 1.5 wt % $CaCl_2$ and polyethyleneimine as hardening solution and 0.05 wt % polylysine solution as coating solution. The concentration of polyethyleneimine, the hardening time and the coating time are set forth in Table 5. The prepared gel-core beads were tested for their mechanical stability by the same method as Example 3 for 48 hours. The test results are summarized in Table 5.

TABLE 5

| polyethyl-eneimine (wt %) | hardening time (minutes) | coating time (minutes) | | |
|---|---|---|---|---|
| | | 6 | 10 | 15 |
| 0.1% | 6 | 0 | 0 | 0 |
| | 10 | 0 | 70 | 99 |
| | 15 | 75 | 95 | 100 |
| 0.5% | 6 | 0 | 0 | 0 |
| | 10 | 7 | 87 | 100 |
| | 15 | 55 | 95 | 100 |
| 1.0% | 6 | 0 | 0 | 0 |
| | 10 | 0 | 78 | 91 |
| | 15 | 75 | 100 | 100 |

*the numeral indicates the percent of gel-core beads remaining unruptured after the shaking test.

As can be seen from Table 5 that if the hardening time and the coating time exceed 10 minutes, most of the prepared gel-core beads remain unruptured. Also, as can be seen from Table 4 and Table 5, if the hardening time and the coating time are within 10 to 15 minutes, the quality of the resulting gel-core beads remains mostly unaffected, indicating the operating of the present method is more flexible than conventional methods.

Example 6

Murein hybridoma CT04 obtained from Veterans General Hospital, Taipei, Taiwan was cultured in a culture medium containing F12:DMEMG(1:1), 10 wt % FCS, penicillin G(100 ng/ml) and streptomycin (100 ng/ml) in T flask. The cultured Murein hybridoma CT04 was then centrifugated with 800×g for 5 minutes, recovered and suspended in an Erlenmeyer flask. A Murein hybridoma CT04 solution with a concentration of 5×10 cells/ml was obtained.

The prepared Murein hybridoma CT04 solution was then encapsulated with various microcapsules. The preparation of these microcapsules are summarized in Table 6 below.

TABLE 6

| | Core Material | hardening Solution | polylysine coating | Citrate Treatment |
|---|---|---|---|---|
| Alginate Gel-beads | 0.9% alginate | 1.5% $CaCl_2$ | 0.05% | no |
| Polylysine-coated liquid-core capsules | 0.9% alginate | 1.5% $CaCl_2$ | 0.05% | yes |
| PEI-reinforced gel-beads | 0.9% alginate | 1.5% $CaCl_2$ + 0.5% PEI | 0.05% | no |
| A Type microcapsules | 0.9% alginate | 1.5% $CaCl_2$ + 0.5% PEI | 0.05% | yes |
| B Type microcapsules | 0.2% alginate + 1.2% CMC | 1.5% $CaCl_2$ + 0.5% PEI | 0.05% | no |

*the concentration indicated in the table is wt %

In the preparation of the above microcapsules, the amount of the core material solution added is 9 times that of the Murein hybridoma CT04 solution. The volume ratio of core material solution to the hardening solution is 1:20, and the volume ratio of the formed gel-core beads to the polylysine solution is also 1:20. The hardening time and the coating time in all the above prepareations are both 6 to 15 minutes.

The encapsulated Murein hybridoma CT04 cells were then placed in T-flasks and incubated in a state of 20 microcapsules per ml of culture medium. The cell concentrations after incubating for 12 days are shown in FIG. 1.

Figure 1:
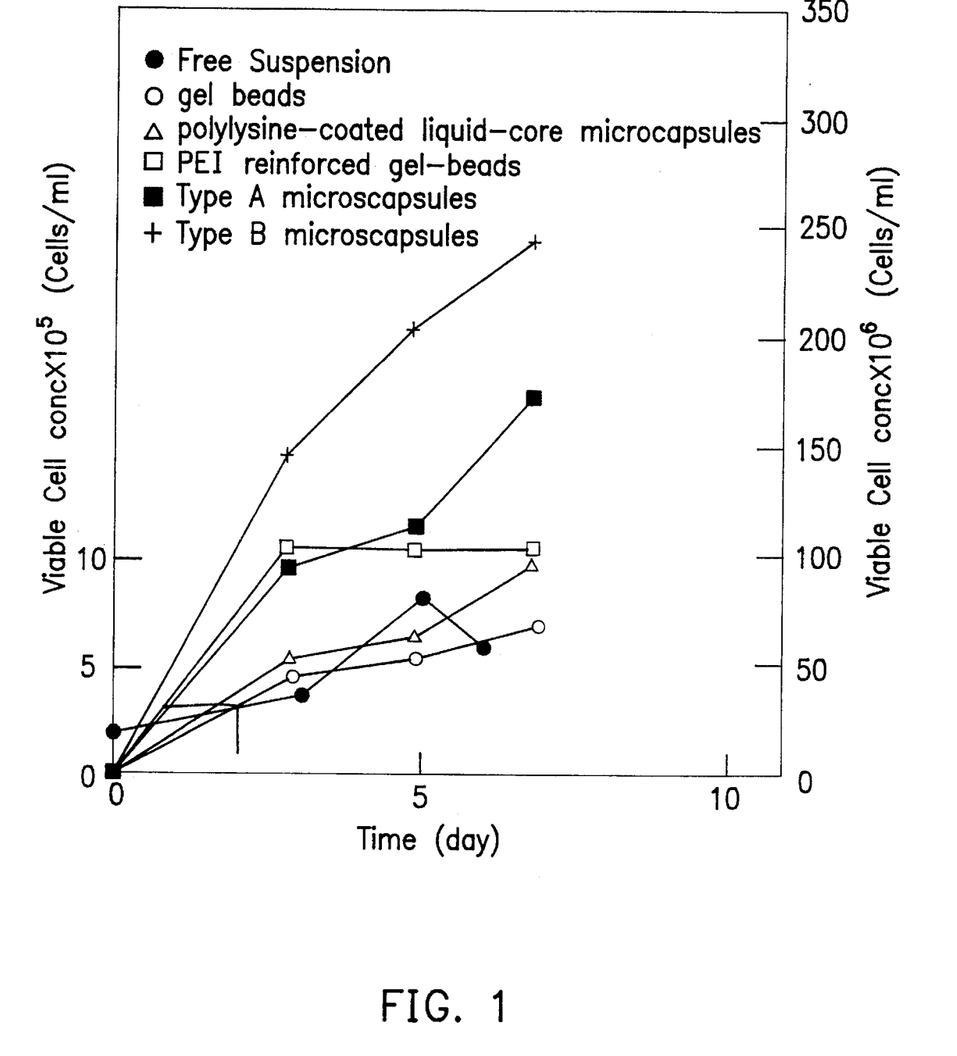
FIG. 1 is a graph showing the viable cell concentration encapsulated in various microcapsules as prepared in Example 6.

As can be seen from FIG. 1, the viable cell concentrations cultivated by using Type A and Type B microcapsules of the invention are higher than that of conventional microcapsules.

Example 7

Gel beads, Type A and Type B microcapsules were prepared by following the procedures of Example 6 except that concentrations of polyethyleneimine (PEI) in the hardening solutions were used as indicated in Table 7 below.

TABLE 7

| PEI in hardening solution (wt %) | Cell Concentration ($10^6$ cells/ml-capsules) | | |
|---|---|---|---|
| | 7th day | 10th day | 12th day |
| gel-core beads | | | |
| 0% | 5 | 5 | 16 |
| 0.1% | 5 | 4 | 10 |
| 0.5% | 10 | 32 | 42 |
| 1.0% | 9 | 17 | 33 |
| A Type | | | |
| 0.1% | 10 | 49 | 73 |
| 0.5% | 16 | 28 | 47 |
| 1.0% | 10 | 21 | 68 |
| B Type | | | |
| 0.5% | 20 | 49 | 70 200* |

*the result of the 15th day

As can be seen from Table 7, by using the microcapsules of the invention, the cell concentrations can reach $2×10^8$ per ml which is far larger than the cell concentration contained by using conventional microcapsules.

Example 8

Type A microcapsules were prepared by adding a mixture containing 1 wt % alginate and the above prepared Murein hybridoma CT04 solutions to a hardening solution containing 1.5 wt % of $CaCl_2$ and 0.1 wt % of polyethylene imine, coating the formed gel-core beads with 0.05 wt % polylysine solution and followed by washing with water and sodium citrate solution.

Figure 4:
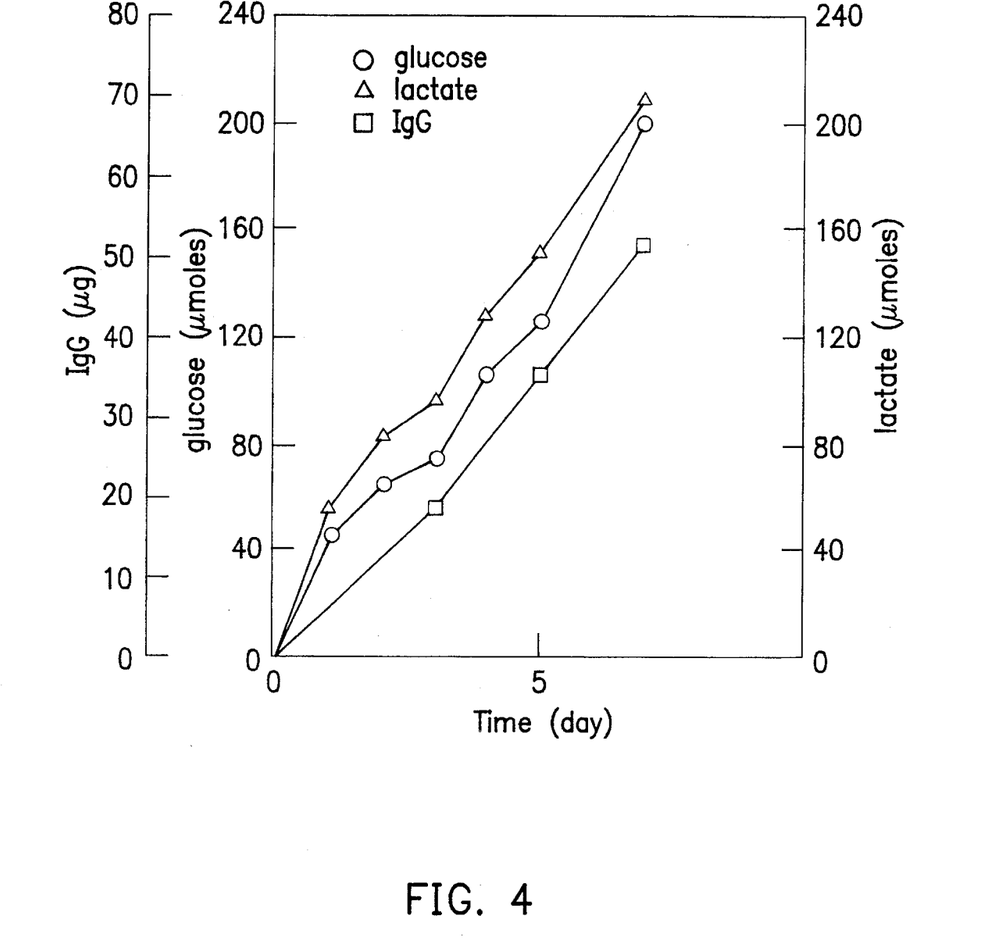
FIG. 4 is a graph showing the amount of glucose uptake, lactate production and IgG production of the cells encapsulated in Type A microcapsules as prepared in Example 8.

The encapsulated Murein hybridoma CT04 cells were then placed in a T-flask and cultivated in a state of 20 microcapsules per ml of culture medium for 10 days. The rate of glucose uptake, lactate prodution and IgG production of Murein hybridoma CT04 cells after the cultivation are shown in Table 8 below. The amount of glucose uptake, lactate production and IgG production from the encapsulated cells is shown in FIG. 4.

Figure 2:
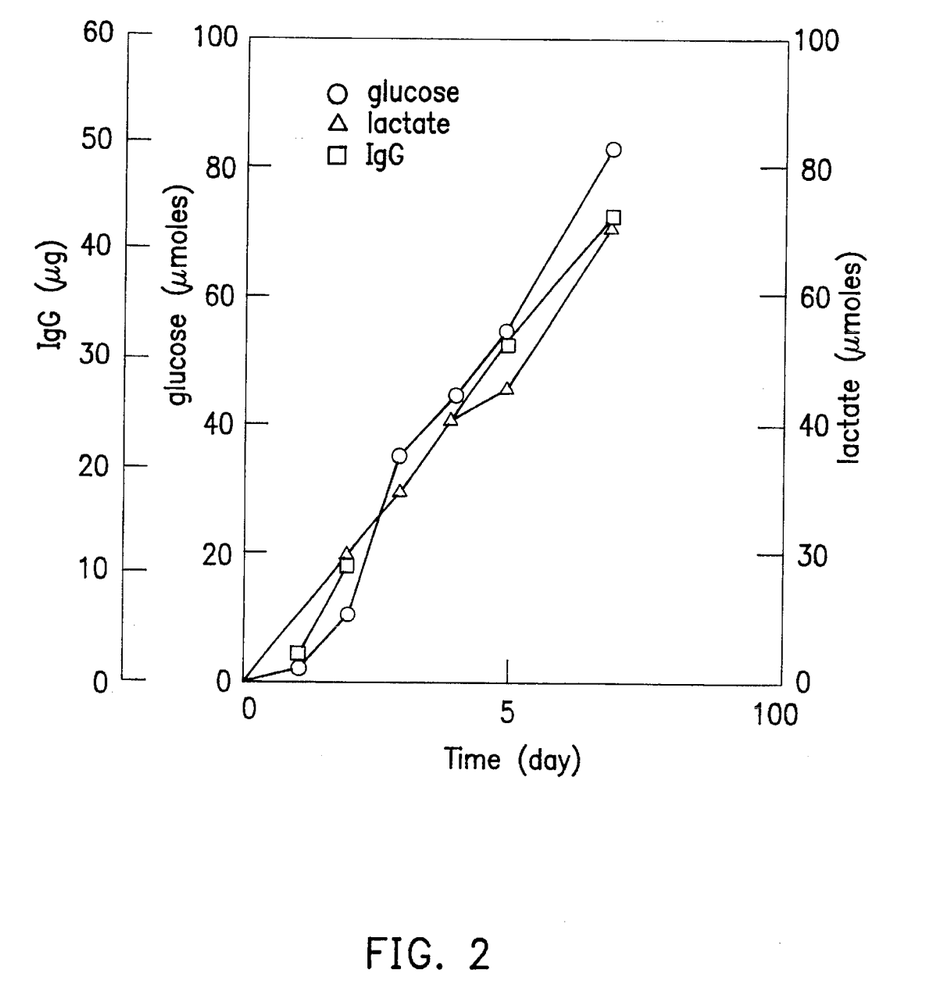
FIG. 2 is a graph showing the amount of glucose uptake, lactate production and IgG production of the cells encapsulated in alginate gel-beads as prepared in Example 6.
Figure 3:
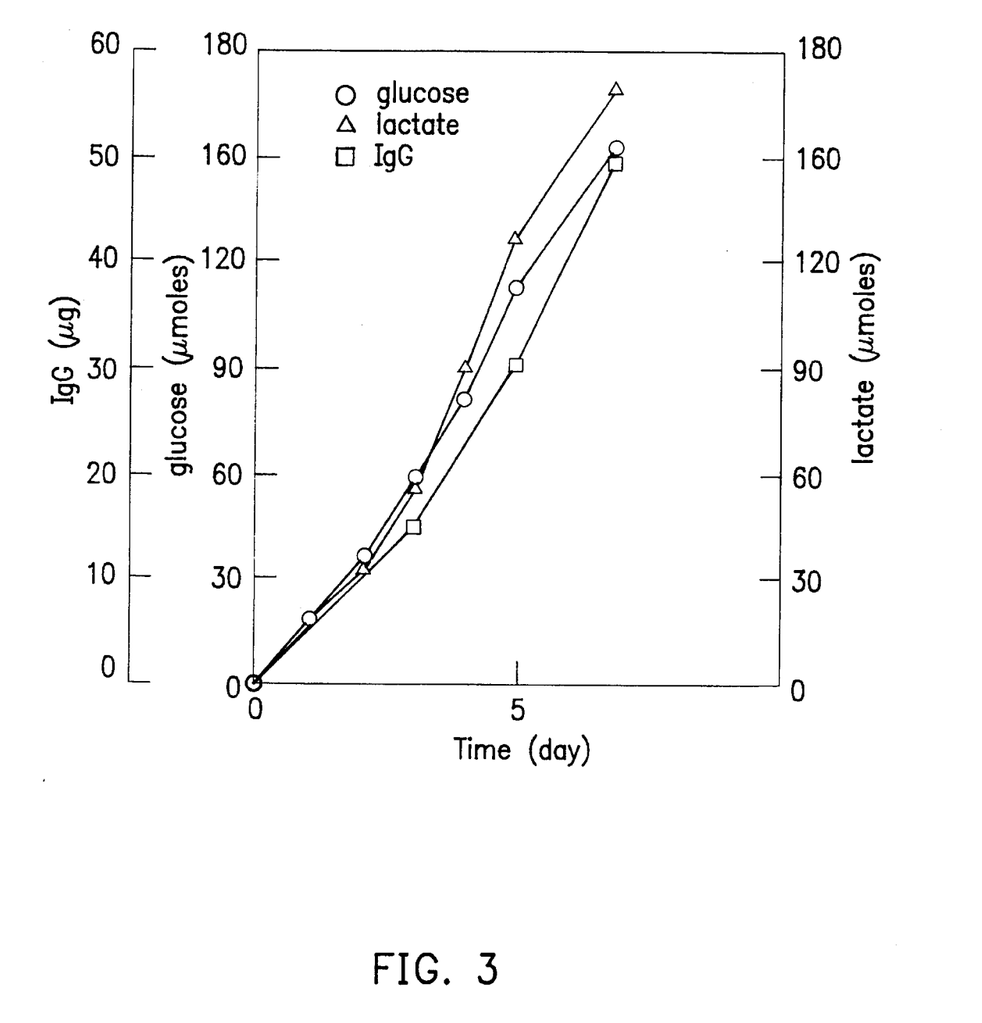
FIG. 3 is a graph showing the amount of glucose uptake, lactate production and IgG production of the cells encapsulated in polylysine coated liquid-core capsules as prepared in Example 6.

The rate of glucose uptake, lactate production and IgG production from the cells encapsulated by alginate gel-beads and polylysine coated liquid-core capsules of Table 6 were measured and also summarized in Table 8. The amount of the glucose uptake, lactate production and IgG production of alginate gel-beads and polylysine coated liquid-core microcapsules are respectively depicted in FIG. 2 and FIG. 3.

Example 9

Type B microcapsules were prepared by adding a mixture containing 1.2 wt of carboxylmethyl cellulose and 0.2 wt % pf alginate and the above prepared Murein hybridoma CT04 solutions to a hardening solution containing 1.5 wt % of $CaCl_2$ and 0.1 wt % of polyethylene imine, coating the formed gel-core beads with 0.05 wt % polylysine solution and followed by washing with water and sodium citrate solution.

Figure 5:
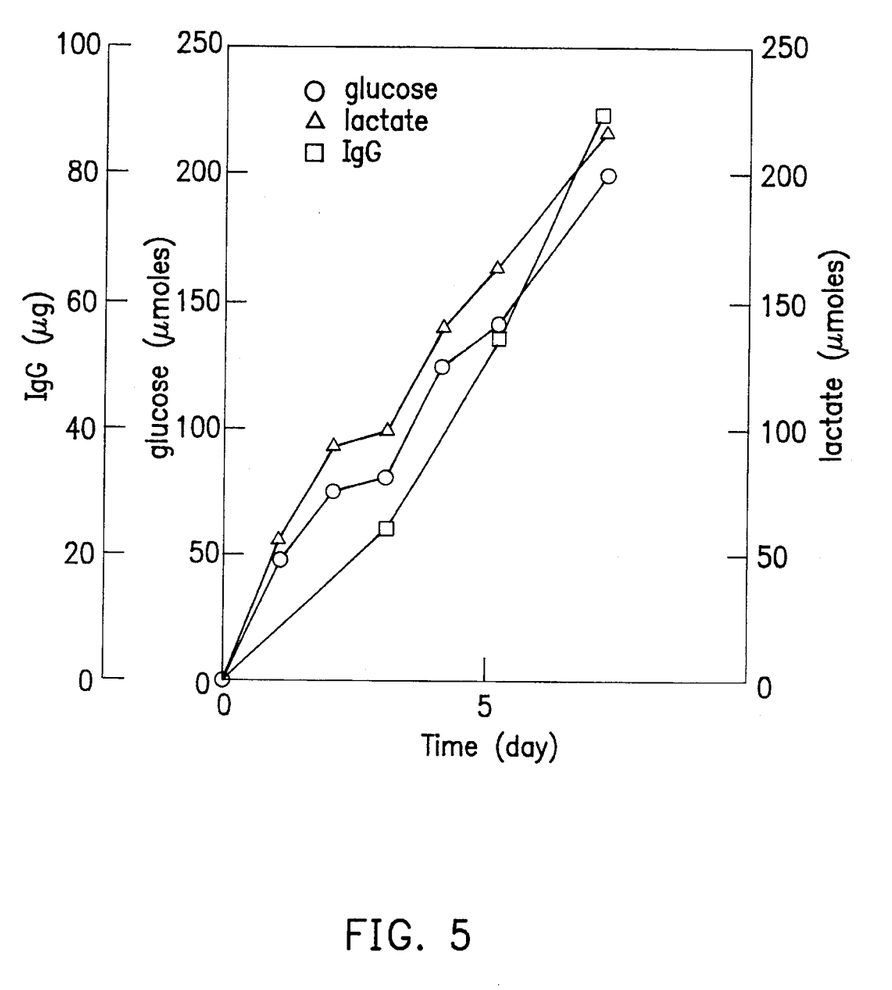
FIG. 5 is a graph showing the amount of glucose uptake, lactate production and IgG production of the cells encapsulated in Type B microcapsules as prepared in Example 9.

The encapsulated Murein hybridoma CT04 cells were then placed in a T-flask and cultivated in a state of 20 microcapsules per ml of culture medium for 10 days. The rate of glucose uptake, lactate prodution and IgG production of Murein hybridoma CT04 cells after the cultivation are shown in Table 8 below. The amount of glucose uptake, lactate production and IgG production from the encapsulated cells is shown in FIG. 5.

TABLE 8

|  | glucose uptake | lactate production | IgG production |
|---|---|---|---|
| Free Suspension | 0.25* | 0.28* | 0.12** |
| Alginate gel-bead | 0.26 | 0.22 | 0.15 |
| Polylysine-coated liquid-core capsules | 0.40 | 0.35 | 0.12 |
| Type A microcapsules | 0.25 | 0.24 | 0.091 |
| Type B microcapsules | 0.16 | 0.20 | 0.090 |

*µmoles/$10^6$ cells-hr
**µg/$10^6$ cells-hr

Example 10

Figure 6:
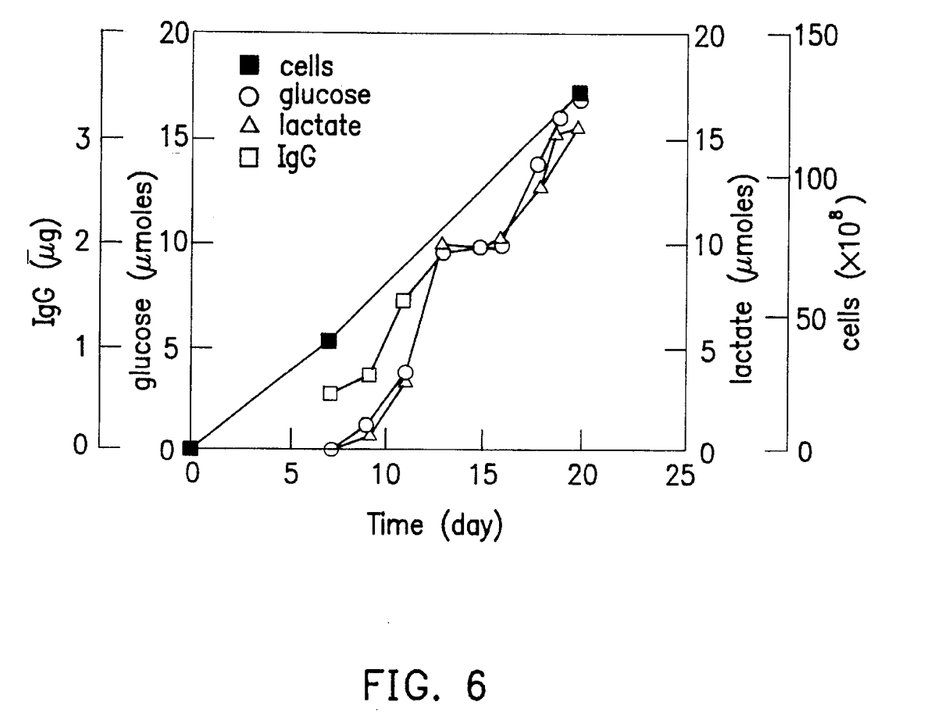
FIG. 6 is a graph showing the amount of glucose uptake, lactate production and IgG production of the cells encapsulated in Type A microcapsules as prepared in Example 8 and cultivated in a one liter reverse funnel-shaped air lift fermenter.

Type A microcapsules prepared in Example 8 were placed in a reverse funnel-shaped air-lift fermenter and incubated at a air flowing rate of 50 ml/min for 21 days. The cell concentration was measured to be $2\times10^8$ cells/ml and no ruptured cells were observed. The amount of the glucose uptake, lactate production and IgG production from the encapsulated Murein hybridoma CT4 cells is shown in FIG. 6.

What is claimed is:

1. A method for preparing liquid-core microcapsules for cell cultures, comprising the following steps:
    (a) adding a core material solution to cultured cells in a culture medium to form a mixture, wherein said core material solution is a solution of alginate;
    (b) adding the mixture to a hardening solution containing $CaCl_2$ and polyethyleneimine to form gel-core beads;
    (c) coating the gel-core beads with a polylysine solution; and
    (d) dissolving the coated gel-core beads with citrate salts to liquify the gel-core beads to form the liquid-core microcapsules.

2. The method as claimed in claim 1, wherein said alginate solution contains 0.2 to 1.0 percent by weight of alginate.

3. The method as claimed in claim 2, wherein said alginate solution contains 0.9 percent by weight of alginate.

4. The method as claimed in claim 1, wherein said hardening solution contains 1 to 3 percent by weight of $CaCl_2$ and 0.1 to 1.5 percent by weight of polyethyleneimine.

5. The method as claimed in claim 4, wherein said hardening solution contains 1.5 percent by weight of $CaCl_2$ and 0.5 percent by weight of polyethyleneimine.

6. The method as claimed in claim 1, wherein said polylysine solution contains 0.05 to 1.0 percent by weight of polylysine.

7. The method as claimed in claim 6, wherein said polylysine solution contains 0.05 percent by weight of polylysine.

8. The method as claimed in claim 1, wherein said citrate salt is sodium citrate.

9. The liquid-core microcapsules for cell cultures prepared by the method as claimed in claim 1.

10. The liquid-core microcapsules for cell cultures prepared by the method as claimed in claim 2.

11. The liquid-core microcapsules for cell cultures prepared by the method as claimed in claim 3.

12. The liquid-core microcapsules for cell cultures prepared by the method as claimed in claim 4.

13. The liquid-core microcapsules for cell cultures prepared by the method as claimed in claim 5.

14. The liquid-core microcapsules for cell cultures prepared by the method as claimed in claim 6.

15. The liquid-core microcapsules for cell cultures prepared by the method as claimed in claim 7.

16. The liquid-core microcapsules for cell cultures prepared by the method as claimed in claim 8.

* * * * *